(12) United States Patent
Stigall et al.

(10) Patent No.: US 11,179,137 B2
(45) Date of Patent: Nov. 23, 2021

(54) TISSUE AND VASCULAR PATHWAY MAPPING USING SYNCHRONIZED PHOTOACOUSTIC AND ULTRASOUND PULLBACK TECHNIQUES

(71) Applicant: KONINKLIJKE PHILIPS N.V., Eindhoven (NL)

(72) Inventors: Jeremy Stigall, Carlsbad, CA (US); Princeton Saroha, Ladera Ranch, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 332 days.

(21) Appl. No.: 16/089,126

(22) PCT Filed: Mar. 28, 2017

(86) PCT No.: PCT/EP2017/057313
§ 371 (c)(1),
(2) Date: Sep. 27, 2018

(87) PCT Pub. No.: WO2017/167751
PCT Pub. Date: Oct. 5, 2017

(65) Prior Publication Data
US 2019/0105015 A1  Apr. 11, 2019

Related U.S. Application Data

(60) Provisional application No. 62/315,176, filed on Mar. 30, 2016.

(51) Int. Cl.
*A61B 8/12* (2006.01)
*A61B 5/00* (2006.01)
*A61B 8/00* (2006.01)

(52) U.S. Cl.
CPC .............. *A61B 8/12* (2013.01); *A61B 5/0035* (2013.01); *A61B 5/0095* (2013.01); *A61B 8/445* (2013.01); *A61B 8/4461* (2013.01); *A61B 8/4416* (2013.01)

(58) Field of Classification Search
CPC ......... A61B 8/12; A61B 5/0035; A61B 8/445; A61B 8/4461; A61B 5/0095; A61B 8/4416
See application file for complete search history.

(56) References Cited

U.S. PATENT DOCUMENTS

2009/0253989 A1  10/2009  Caplan et al.
2011/0021924 A1  1/2011  Sethuraman et al.
(Continued)

*Primary Examiner* — Christopher Koharski
*Assistant Examiner* — Kaitlyn E Selmer (57) ABSTRACT

Imaging devices, systems, and methods are provided. Some embodiments of the present disclosure are particularly directed to imaging a region of interest in tissue with photoacoustic and ultrasound modalities. In some embodiments, a medical sensing system includes one or more external optical emitters and a measurement apparatus configured to be placed within a vascular pathway. The one or more optical emitters and the measurement apparatus may be moved together synchronously. The measurement apparatus may be configured to receive sound waves created by the interaction between emitted optical pulses and tissue, and transmit and receive ultrasound signals. The medical sensing system may also include a processing engine operable to produce images of the region of interest and a display configured to visually display the image of the region of interest.

15 Claims, 7 Drawing Sheets

(56) References Cited

U.S. PATENT DOCUMENTS

| | | | |
|---|---|---|---|
| 2013/0046167 A1* | 2/2013 | Shah | G06K 9/4604 600/407 |
| 2014/0323860 A1* | 10/2014 | Courtney | A61B 8/445 600/427 |
| 2015/0119684 A1* | 4/2015 | Furukawa | A61B 5/004 600/407 |

* cited by examiner

TISSUE AND VASCULAR PATHWAY MAPPING USING SYNCHRONIZED PHOTOACOUSTIC AND ULTRASOUND PULLBACK TECHNIQUES

This application is the U.S. National Phase application under 35 U.S.C. § 371 of International Application No. PCT/EP2017/057313, filed on Mar. 28, 2017, which claims the benefit of Provisional Application Ser. No. 62/315,176, filed Mar. 30, 2016. These applications are hereby incorporated by reference herein.

TECHNICAL FIELD

The present disclosure relates generally to imaging and mapping vascular pathways and surrounding tissue with photoacoustic and ultrasound modalities.

BACKGROUND

Innovations in diagnosing and verifying the level of success of treatment of disease have migrated from external imaging processes to internal diagnostic processes. In particular, diagnostic equipment and processes have been developed for diagnosing vasculature blockages and other vasculature disease by means of ultra-miniature sensors placed upon the distal end of a flexible measurement apparatus such as a catheter, or a guide wire used for catheterization procedures. For example, known medical sensing techniques include angiography, intravascular ultrasound (IVUS), forward looking IVUS (FL-IVUS), fractional flow reserve (FFR) determination, a coronary flow reserve (CFR) determination, optical coherence tomography (OCT), trans-esophageal echocardiography, and image-guided therapy.

For example, intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. There are two general types of IVUS devices in use today: rotational and solid-state (also known as synthetic aperture phased array). For a typical rotational IVUS device, a single ultrasound transducer element is located at the tip of a flexible driveshaft that spins inside a plastic sheath inserted into the vessel of interest. In side-looking rotational devices, the transducer element is oriented such that the ultrasound beam propagates generally perpendicular to the longitudinal axis of the device. In forward-looking rotational devices, the transducer element is pitched towards the distal tip so that the ultrasound beam propagates more towards the tip (in some devices, being emitted parallel to the longitudinal centerline). The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS medical sensing system assembles a two dimensional display of the tissue, vessel, heart structure, etc. from a sequence of pulse/acquisition cycles occurring during a single revolution of the transducer. In order to image a length of a vessel, the transducer element is drawn through the vessel as it spins.

In contrast, solid-state IVUS devices utilize a scanner assembly that includes an array of ultrasound transducers connected to a set of transducer controllers. In side-looking and some forward-looking IVUS devices, the transducers are distributed around the circumference of the device. In other forward-looking IVUS devices, the transducers are a linear array arranged at the distal tip and pitched so that the ultrasound beam propagates closer to parallel with the longitudinal centerline. The transducer controllers select transducer sets for transmitting an ultrasound pulse and for receiving the echo signal. By stepping through a sequence of transmit-receive sets, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state scanner can be wired directly to the medical sensing system with a simple electrical cable and a standard detachable electrical connector. While the transducers of the scanner assembly do not spin, operation is similar to that of a rotational system in that, in order to image a length of a vessel, the scanner assembly is drawn through the vessel while stepping through the transmit-receive sets to produce a series of radial scans.

Rotational and solid-state state IVUS are merely some examples of imaging modalities that sample a narrow region of the environment and assemble a two- or three-dimensional image from the results. Other examples include optical coherence tomography (OCT), which has been used in conjunction with ultrasound systems. One of the key challenges using these modalities with in a vascular pathway is that they are limited in gathering data on anatomy beyond the vessel walls. Although OCT imaging may yield higher resolution than IVUS imaging, OCT has particularly limited penetration depth and may take more time to image a region of tissue.

Another recent biomedical imaging modality is photoacoustic imaging. Photoacoustic imaging devices deliver a short laser pulse into tissue and monitor the resulting acoustic output from the tissue. Due to varying optical absorption throughout the tissue, pulse energy from the laser pulse causes differential heating in the tissue. This heating and associated expansion leads to the creation of sound waves corresponding to the optical absorption of the tissue. These sound waves can be detected and an image of the tissue can be generated through analysis of the sound waves and associated vascular structures can be identified, as described in U.S. Patent Publication 2013/0046167 titled "SYSTEMS AND METHODS FOR IDENTIFYING VASCULAR BORDERS," which is hereby incorporated by reference in its entirety.

Accordingly, for these reasons and others, the need exists for improved systems and techniques that allow for the mapping of vascular pathways and surrounding tissue.

SUMMARY

Embodiments of the present disclosure provide a mapping system that combines photoacoustic and IVUS imaging system. The system may be used to map vascular pathways and surrounding tissue.

In some embodiments, a medical sensing system is provided comprising: an optical emitter configured to emit optical pulses to tissue in a region of interest, wherein the optical emitter is connected to an actuator; and a measurement apparatus configured to be placed within a vascular pathway in the region of interest, wherein the measurement apparatus is connected to a pullback device; wherein the actuator and the pullback device are configured to coordinate movements of the optical emitter and the measurement apparatus.

In some embodiments, the measurement apparatus is configured to: receive sound waves generated by the tissue as a result of interaction of the optical pulses with the tissue; transmit ultrasound signals; and receive ultrasound echo signals based on the transmitted ultrasound signals. The system may comprise a processing engine in communication with the measurement apparatus, the processing engine operable to produce an image of the region of interest based on the received sound waves and the received ultrasound echo signals. The system may comprise a display in communication with the processing engine, the display configured to visually display the image of the region of interest.

In some embodiments, the actuator is in communication with the pullback device. The actuator and pullback device may move the optical emitter and the measurement apparatus together. Furthermore, the actuator and pullback device may move the optical emitter and the measurement apparatus together with synchronized movements. The system may also include a controller operable to control the actuator and the pullback device. The controller may be further operable to synchronize movements of the optical emitter and the measurement apparatus. In some embodiments, the measurement apparatus further comprises at least one ultrasound transducer configured to transmit ultrasound signals and receive ultrasound echo signals based on the transmitted ultrasound signals. The at least one ultrasound transducer may be further configured to receive sound waves generated by the tissue as a result of interaction of the optical pulses with the tissue.

In some embodiments, the measurement apparatus further comprises at least one photoacoustic transducer configured to receive sound waves generated by the tissue as a result of interaction of the optical pulses with the tissue. The at least one photoacoustic transducer and the at least ultrasound transducer may be configured to alternate in receiving sound waves and ultrasound echo signals. The at least one photoacoustic transducer may be disposed circumferentially around a distal portion of the measurement apparatus. The at least one photoacoustic transducer may be coupled to a drive member that rotates the at least one transducer around a longitudinal axis of the measurement apparatus.

In some embodiments, a method of mapping a region of interest is provided, comprising: transmitting, with a laser source disposed outside a body of a patient, focused laser pulses on tissue in a region of interest having a vascular pathway as the laser source is moved along a first path outside the body of the patient; receiving, with at least one photoacoustic sensor positioned within the vascular pathway of the region of interest, sound waves generated by the interaction of the focused laser pulse with the tissue as the at least one photoacoustic sensor is moved along a second path within the vascular pathway; producing an image of the region of interest based on the received sound waves; and outputting the image of the region of interest to a display.

In some embodiments, the first path is linear. The first path may also be non-linear or arcuate. In some embodiments, the second path is linear. The second path may also be non-linear or arcuate. The method may also comprise transmitting, with at least one ultrasound transducer positioned within the vascular pathway of the region of interest, ultrasound signals toward the tissue in the region of interest; and receiving, with the at least one ultrasound transducer positioned within the vascular pathway of the region of interest, ultrasound echo signals of the transmitted ultrasound signals.

In some embodiments, the step of producing an image of the region of interest is based on the received sound waves and the received ultrasound echo signals. A controller may transmit control signals to one or more actuators to selectively control movement of the laser source and a measurement apparatus that includes the at least one photoacoustic sensor. The controller may synchronize the movement of the laser source and the at least one photoacoustic sensor. In some embodiments, the controller accounts for difference in length between the first path and the second path.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the intravascular sensing system is described in terms of cardiovascular imaging, it is understood that it is not intended to be limited to this application. The system is equally well suited to any application requiring imaging within a lumen or cavity of a patient. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1A:
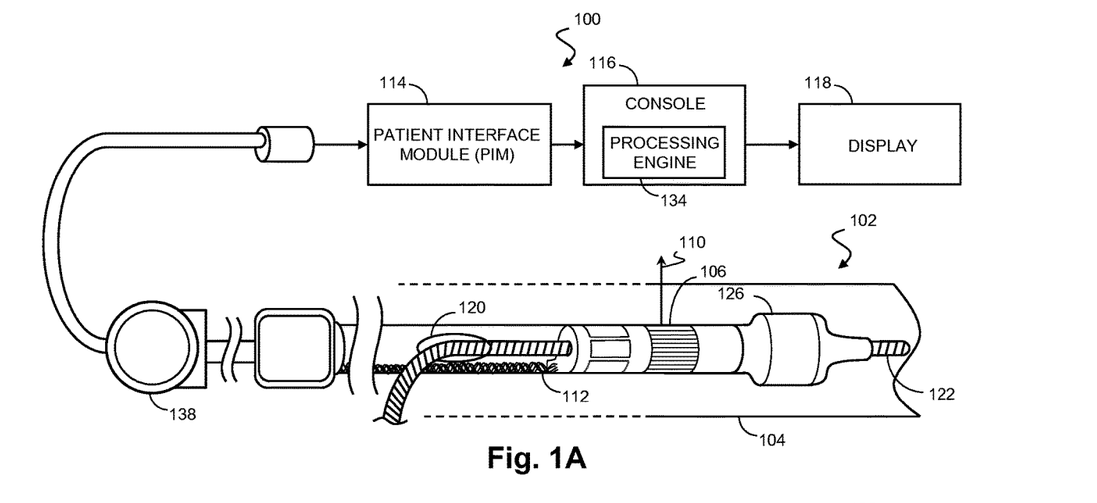
FIG. 1A is a diagrammatic schematic view of a medical sensing system according to some embodiments of the present disclosure.

FIG. 1A is a diagrammatic schematic view of a medical sensing system 100 according to some embodiments of the present disclosure. The medical sensing system 100 includes a measurement apparatus 102 (such as a catheter, guide wire, or guide catheter). As used herein, "measurement apparatus" or "flexible measurement apparatus" includes at least any thin, long, flexible structure that can be inserted into the vasculature of a patient. While the illustrated embodiments of the "measurement apparatus" of the present disclosure have a cylindrical profile with a circular cross-sectional profile that defines an outer diameter of the flexible measurement apparatus 102, in other instances, all or a portion of the flexible measurement apparatus 102 may have other geometric cross-sectional profiles (e.g., oval, rectangular, square, elliptical, etc.) or non-geometric cross-sectional profiles. Flexible measurement apparatus 102 may include, for example, guide wires, catheters, and guide catheters. In that regard, a catheter may or may not include a lumen extending along all or a portion of its length for receiving and/or guiding other instruments. If the catheter includes a lumen, the lumen may be centered or offset with respect to the cross-sectional profile of the device.

The medical sensing system 100 may be utilized in a variety of applications and can be used to assess vascular pathways and structures within a living body. To do so, the measurement apparatus 102 is advanced into a vascular passage 104. The vascular passage 104 represents fluid filled or surrounded structures, both natural and man-made, within a living body that may be imaged and can include for example, but without limitation, structures such as: organs including the liver, heart, kidneys, as well as valves within the blood or other systems of the body. In addition to imaging natural structures, the images may also include man-made structures such as, but without limitation, heart valves, stents, shunts, filters and other devices positioned within the body. The measurement apparatus 102 includes one or more sensors 106 disposed along the length of the apparatus 102 to collect diagnostic data regarding the vascular pathway 104. In various embodiments, the one or more sensors 106 correspond to sensing modalities such as IVUS imaging, pressure, flow, OCT imaging, transesophageal echocardiography, temperature, other suitable modalities, and/or combinations thereof.

In the exemplary embodiment of FIG. 1A, the measurement apparatus 102 includes a solid-state IVUS device, and the sensors 106 include one or more IVUS ultrasound transducers and/or photoacoustic transducers and associated control. As used herein, a "photoacoustic transducer" includes at least a sensor configured to detect photoacoustic waves generated as a result of the interaction of optical pulses with tissue. In one embodiment, a photoacoustic transducer utilizes the same ultrasound detection mechanism as an IVUS ultrasound transducer. In some implementations, a single transducer can serve as both an IVUS transducer and a photoacoustic transducer. In another embodiment, a photo acoustic transducer uses a dedicated photoacoustic wave detection mechanism distinct from that of an IVUS ultrasound transducer. In another embodiment, a photoacoustic transducer uses a dedicated photoacoustic wave detection mechanism distinct from that of an IVUS ultrasound transducer. The system of FIG. 1A may include aspects of phased-array IVUS devices, systems, and methods associated with the Eagle Eye® Platinum catheter available from Volcano Corporation as well as those described in U.S. Pat. No. 7,846,101 and/or U.S. patent application Ser. No. 14/812,792, filed Jul. 29, 2015, each of which is hereby incorporated by reference in its entirety.

The sensors 106 may be arranged around the circumference of the measurement apparatus 102 and positioned to emit ultrasound energy radially 110 in order to obtain a cross-sectional representation of the vascular pathway 104 and the surrounding anatomy. When the sensors 106 are positioned near the area to be imaged, the control circuitry selects one or more IVUS transducers to transmit an ultrasound pulse that is reflected by the vascular pathway 104 and the surrounding structures. The control circuitry also selects one or more transducers to receive the ultrasound echo signal. By stepping through sequences of transmit-receive sets, the medical sensing system 100 system can synthesize the effect of a mechanically scanned transducer element without moving parts.

In one embodiment, the sensors 106 are disposed circumferentially around a distal portion of the measurement apparatus 102. In another embodiment, the sensors 106 are contained within the body of the measurement apparatus 102. In other embodiments, the sensors 106 are disposed radially across the measurement apparatus 102, on a movable drive member connected to the measurement apparatus 102, or on one or more planar arrays connected to the measurement apparatus 102.

In some embodiments, the processing engine 134, which may be included in the console 116, combines the imaging data acquired from both the IVUS and photoacoustic modalities into a single visualization. This use of both IVUS and photoacoustic modalities may provide a number of advantages over traditional systems using a single modality. First, the addition of photoacoustic sensors may allow for higher resolution mapping than traditional IVUS methods alone. Second, the combination of IVUS and photoacoustic modalities may allow for faster imaging speeds than OCT imaging or other methods. Third, the combination may allow for two-dimensional and/or three-dimensional imaging of the tissue surrounding vascular pathways. Fourth, the use of photoacoustic imaging may expand the diagnostic scope of an IVUS mapping procedure by including more of the surrounding tissue. In particular, the combined IVUS and photoacoustic mapping can allow for detection of certain types of cancers, tissue damage, and the mapping of multiple vascular pathways without sacrificing the dependability of ultrasound in detecting plaques, stenosis, and other forms of vascular diseases. Fifth, combining these two modalities may allow substantial costs savings because existing IVUS systems may be adapted to mapping systems using both modalities. Sixth, due to the interaction of optical pulses with tissue and the omni-directional emission of photoacoustic waves from the tissue, an optical pulse need not be emitted along the same axis as the transducer. This allows for more flexibility in carrying out combined photoacoustic and IVUS procedures, and may allow for precise mapping procedures even along deep or convoluted vascular pathways. Seventh, the mapping capabilities of the present disclosure may be integrated with some forms of laser therapy. For example, diagnosis of diseases in tissue may be accomplished using the optical emitter in diagnostic mode. After a diagnosis, the optical emitter can be switched to a treatment mode. In this regard, the map of the vasculature and surrounding tissue may be used to guide the application of the treatment. After the optical treatment is finished, the optical emitter can be switched back to diagnostic mode to confirm treatment of the diseased portion of tissue.

Sensor data may be transmitted via a cable 112 to a Patient Interface Module (PIM) 114 and to console 116, as well as to the processing engine 134 which may be disposed within the console 116. Data from the one or more sensors 106 may be received by a processing engine 134 of the console 116. In other embodiments, the processing engine 134 is physically separated from the measurement apparatus 102 but in communication with the measurement apparatus (e.g., via wireless communications). In some embodiments, the processing engine 134 is configured to control the sensors 106. Precise timing of the transmission and reception of signals may be used to map vascular pathways 104 in procedures using both IVUS and photoacoustic modalities. In particular, some procedures may involve the activation of sensors 106 to alternately transmit and receive signals. In systems using one or more IVUS transducers that are configured to receive both photoacoustic and ultrasound signals, the processing engine 134 may be configured to control the state (e.g., send/receive) of one or more transducers during the mapping of the vascular pathway and surrounding tissue.

Moreover, in some embodiments, the processing engine 134, PIM 114, and console 116 are collocated and/or part of the same system, unit, chassis, or module. Together the processing engine 134, PIM 114, and/or console 116 assemble, process, and render the sensor data for display as an image on a display 118. For example, in various embodiments, the processing engine 134, PIM 114, and/or the console 116 generates control signals to configure the sensor 106, generates signals to activate the sensor 106, performs amplification, filtering, and/or aggregating of sensor data, and formats the sensor data as an image for display. The allocation of these tasks and others can be distributed in various ways between the processing engine 134, PIM 114, and the console 116.

Sill referring to FIG. 1A, a pullback device 138 may be connected to the measurement apparatus 102. In some embodiments, the pullback device 138 is configured to pull a measurement apparatus 102 through a vascular pathway 104. The pullback device 138 may be configured to pull the measurement apparatus at one or more fixed velocities and/or fixed distances. In other instances, the pullback device 138 may be configured to pull the measurement apparatus at variable speeds and/or variable distances. The pullback device 138 may be selectively connected to the measurement apparatus 102 by mechanical connections such as male/female plug interactions, mechanical couplings, fasteners, and/or combinations thereof. Further, in some instances the pullback device 138 may be mechanically coupled and/or integrated with the PIM 114. In such instances, connection of the measurement apparatus 102 to the PIM 114 can couple the pullback device 138 to the measurement apparatus 102. The pullback device 138 may be slid across a cable, track, wire, or ribbon. In some embodiments, the pullback device 138 is in communication with one or more of a processing engine 134, a PIM 114, or a console 116. Furthermore, the pullback device 138 may be controlled by signals sent through a processing engine 134, a PIM 114, or a console 116. The pullback device 138 may also be placed in communication with another motivation device such as an actuator to drive an external optical emitter. In some embodiments, an actuator is synched with the pullback device 138 to synchronously move an external optical emitter and a measurement apparatus 102.

In addition to various sensors 106, the measurement apparatus 102 may include a guide wire exit port 120 as shown in FIG. 1A. The guide wire exit port 120 allows a guide wire 122 to be inserted towards the distal end in order to direct the member 102 through a vascular structure (i.e., the vascular pathway) 104. Accordingly, in some instances the measurement apparatus 102 is a rapid-exchange catheter. Additionally or in the alternative, the measurement apparatus 102 can be advanced through the vascular pathway 104 inside a guide catheter 124. In an embodiment, the measurement apparatus 102 includes an inflatable balloon portion 126 near the distal tip. The balloon portion 126 is open to a lumen that travels along the length of the IVUS device and ends in an inflation port (not shown). The balloon 126 may be selectively inflated and deflated via the inflation port. In other embodiments, the measurement apparatus 102 does not include balloon portion 126.

Figure 1B:
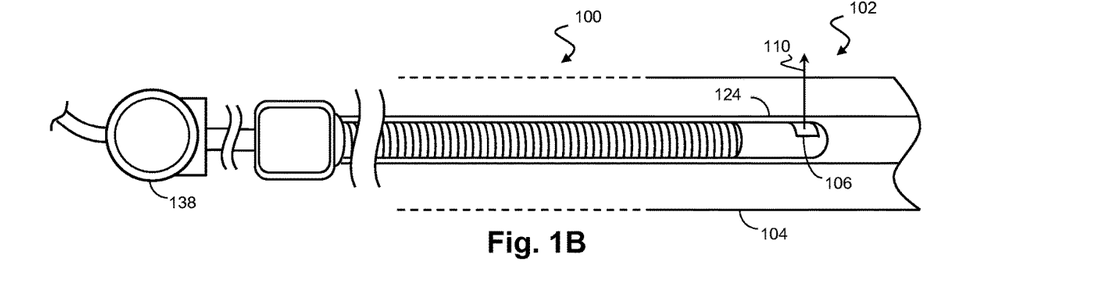
FIG. 1B is a diagrammatic schematic view of a medical sensing system according to some embodiments of the present disclosure.

FIG. 1B is a schematic view of a system that includes an alternative measurement apparatus 102 according to some embodiments of the present disclosure. The measurement apparatus 102 of FIG. 1B is typical of a rotational device such as a rotational IVUS ultrasound system and the one or more sensors 106 include one or more IVUS transducers arranged to emit ultrasound energy in a radial direction 110, as well as one or more photoacoustic transducers. Again, a single transducer may serve as both an IVUS transducer and a photoacoustic transducer. In such an embodiment, the one or more sensors 106 may be mechanically rotated around a longitudinal axis of the measurement apparatus 102 to obtain a cross-sectional representation of the vascular pathway 104. The system of FIG. 1B may include aspects of rotational IVUS devices, systems, and methods associated with the Revolution® catheter available from Volcano Corporation as well as those described in U.S. Pat. Nos. 5,243,988, 5,546,948, and 8,104,479 and/or U.S. patent application Ser. No. 14/837,829, filed Aug. 27, 2015, each of which is hereby incorporated by reference in its entirety.

Figure 1C:
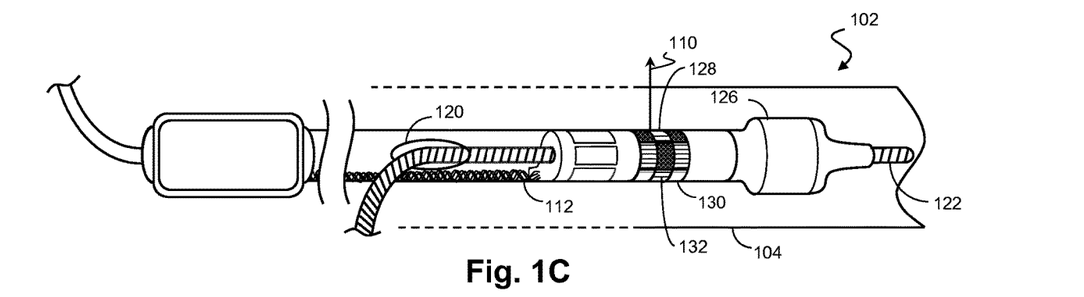
FIG. 1C is a diagrammatic schematic view of a medical sensing system with an exemplary sensor array according to some embodiments of the present disclosure.
Figure 1D:
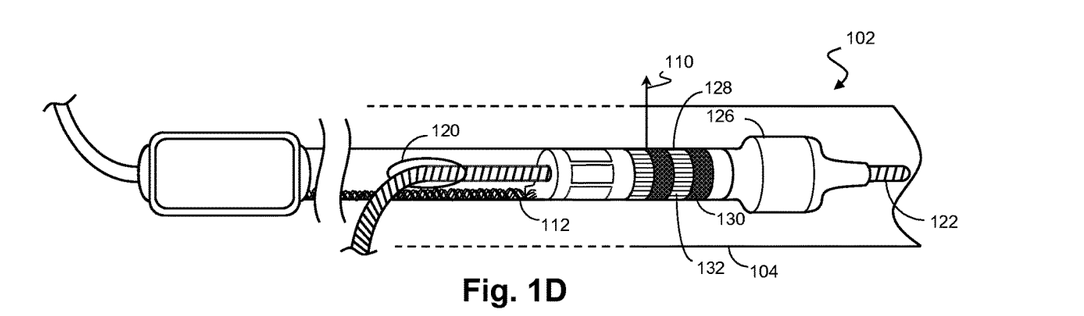
FIG. 1D is a diagrammatic schematic view of a medical sensing system with another exemplary sensor array according to some embodiments of the present disclosure.

FIGS. 1C and 1D show alternative sensor arrays 128 that may be used in conjunction with the measurement apparatus 102 according to some embodiments of the present disclosure. In particular, the sensor array 128 may include one or more sensors 106 and emitters including IVUS transducers, IVUS emitters, photoacoustic transducers, and optical emitters. In FIG. 1C, the sensor array 128 is disposed around the circumference of the measurement apparatus 102. Sensors 106 of two more different types are placed in the sensor array 128. In particular, sensors of a first type 130 are placed in the sensor array 128 with sensors of a second type 132. In the example of FIG. 1C, the sensors of the first and second types 130, 132 are disposed on the array 128 in an alternating manner. In some embodiments, sensors of the first and second types 130, 132 are disposed on the array 128 in a checkerboard configuration such that individual sensors of the first type 130 are not adjacent to each other. Additionally, sensors of the first and second types 130, 132 may take up roughly equal proportions of the area of the array 128. Although they appear as square or rectangular in the example of FIG. 1C, sensors of the first and second types 130, 132 may have circular, elliptical, polygonal, or other shapes. Sensors of the first and second types 130, 132 may be spaced across the measurement apparatus 102 or they may be placed flush against each other.

In the example of FIG. 1D, a sensor array 128 is shown with sensors of two or more different types 130, 132 disposed in alternating rows. These rows may be disposed radially and may extend part way or completely around the measurement apparatus 102. In some embodiments, rows of sensors placed in a staggered formation such that the ends of individual rows are not co-terminus. In some embodiments, rows of sensors are placed adjacent to each other with no space in between. Alternatively, rows of sensors are spaced across the measurement apparatus 102 with space therebetween. In some cases, 2, 3, 4, or 5 rows of alternating sensors are disposed on the measurement apparatus 102. As discussed above, the array 128 may be configured to rotate around an axis of the measurement apparatus 102.

The systems of the present disclosure may also include one or more features described in U.S. Provisional Patent Application Nos. 62/315,117, 62/315,220, 62/315,251, and/or 62/315,275, each of which was filed on Mar. 30, 2016 and incorporated by reference in its entirety.

Figure 2:
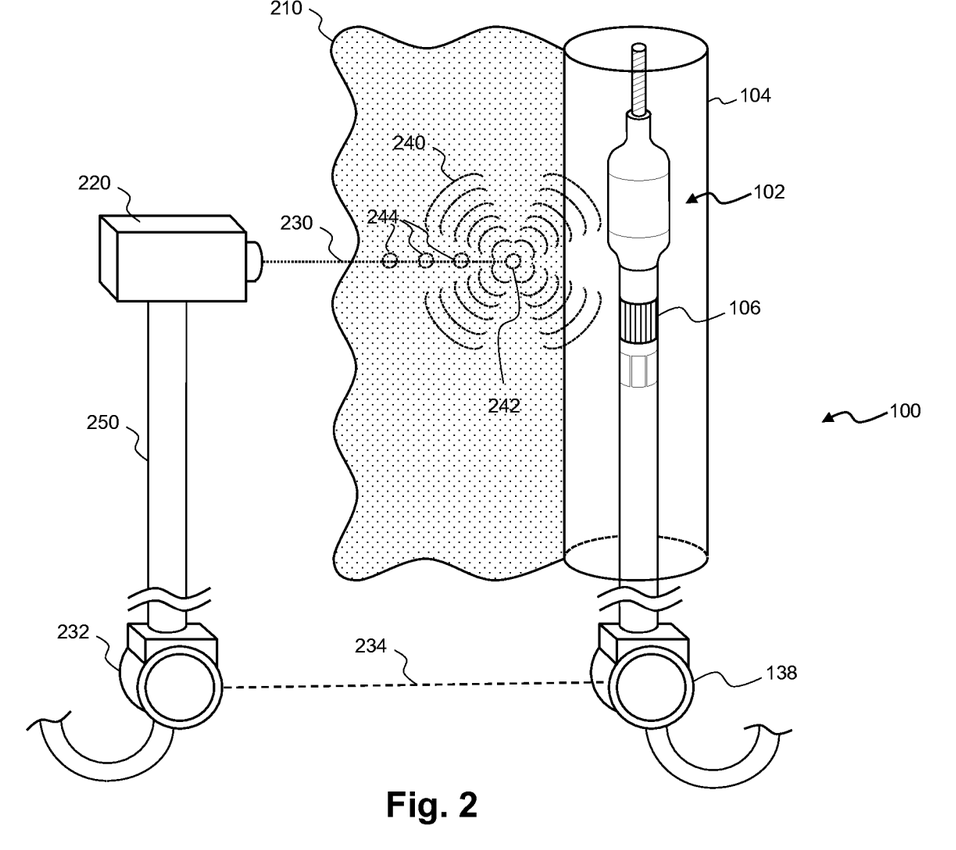
FIG. 2 is a diagrammatic, perspective view of a vascular pathway and surrounding tissue with an instrument positioned within the pathway and an external emitter according to an embodiment of the present disclosure.

FIG. 2 is a diagrammatic, perspective view of a vascular pathway 104 and surrounding tissue 210 with a measurement apparatus 102 such as that depicted in FIGS. 1A-1D disposed within the vascular pathway 104. An optical emitter 220 is also shown emitting an optical pulse 230 toward an area of interest within the tissue. In some embodiments, the area of interest includes part of a vascular pathway 104 as well as adjacent tissue. In some embodiments, the optical emitter 220 is a laser source that emits short laser pulses toward the area of interest. These laser pulses interact with the tissue 210 at a focus 242, generating a series of photoacoustic waves 240 that propagate through the tissue 210 and the vascular pathway 104. The photoacoustic waves 240 are received by the sensors 106 connected to the measurement apparatus 102. The sensors 106 may also image and/or map the vascular pathway 104 independently of the photoacoustic waves 240 by transmitting ultrasound signals toward the vascular pathway walls and receiving the corresponding reflected ultrasound echo signals.

An operator may move the measurement apparatus 102 through the vascular pathway 104 to image and/or map the vascular pathways 104. In some cases, the optical emitter 220 is configured to emit optical pulses 230 toward the sensors 106 of the measurement apparatus. The optical emitter 220 may also be moved externally in a way that corresponds to the movements of the measurement apparatus 102 so that the measurement apparatus 102 receives photoacoustic waves along the length of the vascular pathway 104. In some embodiments, the optical emitter 220 is moved at a similar speed and direction as the measurement apparatus 102. In some embodiments, the measurement apparatus 102 is moved by a pullback device 138 that is attached to an end of the measurement apparatus. This pullback device may be the pullback device 138 of FIGS. 1A and 1B.

In some embodiments, an actuator 232 is connected to the optical emitter 220 by a connector 250. In some cases, this actuator 232 may be a pullback device, and the connector 250 may be a fastening device. In other cases, the connector 250 is a rigid device such as a rigid elongate member, such as a rod, bar, frame, etc. The connector 250 may be selectively coupled to the optical emitter 220 and actuator 232 by mechanical connections such as male/female plug interactions, mechanical couplings, fasteners, and/or combinations thereof. Alternatively, the connector 250 may be permanently attached and/or integrally formed with one or more of the actuator 232 and/or the optical emitter 220. The actuator 232 may be mechanically coupled to the pullback device 138 so that the actuator 232 and pullback device 138 move with corresponding movements. In some embodiments, the actuator 232 is configured to travel with the optical emitter 220. Additionally, the actuator 232 and optical emitter 220 may be configured to travel along a track, frame, or wire disposed outside the patient's body.

The actuator 232 and pullback device 138 (connected to the measurement apparatus 102) may be synched together to move the optical emitter 220 and measurement apparatus 106 together. In some cases, the actuator 232 and pullback device 138 are in communication with a control device. This control device may send the actuator 232 and pullback device 138 signals to synchronize their movements. Alternatively, the actuator 232 and pullback device 138 communicate directly to one another to provide for synchronized movements of the optical emitter 220 and measurement apparatus 102. Synchronous movements may describe two or more objects moving in an identical direction with the same velocity. However, synchronous movements may also describe two or more objects moving in a corresponding manner, while not in an identical direction or with the same velocity. In some cases, corresponding motions can be applied to objects to move them together in some way. For example, a measurement apparatus 102 may be moved through a convoluted vascular pathway while an external optical emitter 220 is moved linearly along the outside of a patient's body. In this case, the motions of the measurement apparatus 102 and optical emitter 220 correspond but are not identical. The measurement apparatus 102 and optical emitter 220 may travel in different directions and at different velocities while still being synchronized. In some embodiments, movements between the optical emitter 220 and the measurement apparatus 102 allow the measurement apparatus 102 to receive photoacoustic waves along a mapping route through a vascular pathway. In some embodiments, the measurement apparatus 102 and optical emitter 220 are moved so that they stay within an operable zone. More specifically, the operable zone may be defined as an area where sound waves 240 created as a result of the optical pulses 230 may be received by the sensors 106 of the measurement device 102. Synchronized movements will be explained further in reference to FIGS. 3-5.

In some cases, the distance that an optical pulse 230 travels through tissue may be controlled by varying the frequency and length of the pulse. In the example of FIG. 2, the optical emitter 220 may be controlled to produce optical pulses 230 that penetrate tissue 210 at different depths 244. Control over the penetration depth of optical pulses 230 may allow an operator to achieve a more complete map of a vascular pathway and surrounding tissue.

Figure 3:
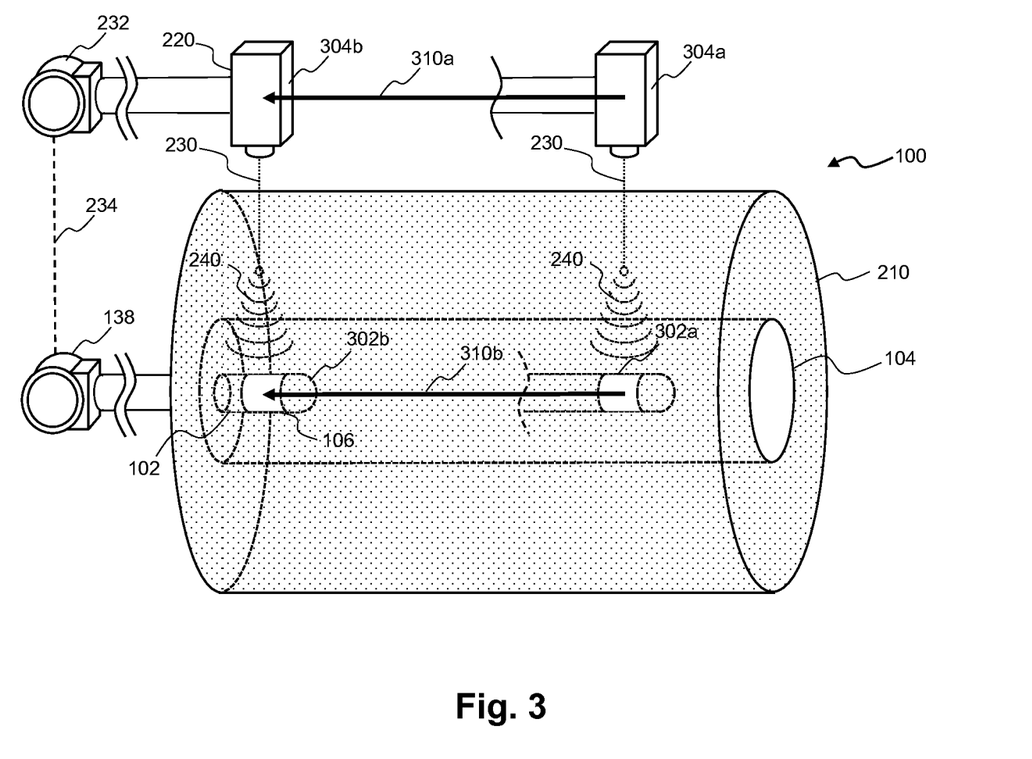
FIG. 3 is a diagrammatic, perspective view of a vascular pathway and surrounding tissue with an instrument moving within the pathway and a moving external emitter according to an embodiment of the present disclosure.

FIG. 3 depicts a measurement apparatus 102 disposed within a vascular pathway 104 and an external optical emitter 220. The measurement apparatus 102 can include one or more sensors 106. In some cases, the sensors 106 rotate around the longitudinal axis of the measurement apparatus 102. An actuator 232 may be connected to and operative to move the optical emitter 220. A pullback device 138 may be connected to and operative to move the measurement apparatus 102. The actuator 232 and pullback device 138 may be in communication, as depicted by the dotted line 234. As discussed above, the actuator 232 and the pullback device 138 may be connected through an external control device, such as a processing engine 134, a PIM 114, or a console 116. Additionally or alternatively, the actuator 232 and the pullback device 138 may be in direct communication. The movements of the optical emitter 220 and measurement apparatus 102 may be synchronized. In the example of FIG. 3, the optical emitter 220 and the measurement apparatus 102 are placed at first position 304a and first position 302a, respectively. The actuator 232 drives the optical emitter 220 to second position 304b along the direction of travel 310a while the pullback device 138 moves the measurement apparatus 102 to second position 302b along the direction of travel 310b. In this case, direction 310a is equivalent to direction 310b due to the relatively straight vascular pathway 104 through which the measurement apparatus 102 travels. In some cases, the movement of the optical emitter 220 and the measurement apparatus 102 may occur at the same time. It is noted that photoacoustic waves 240 reach the sensor array 106 connected to the measurement apparatus 102 at the first position 302a and the second position 302b as well as intermediate positions therebetween.

Figure 4:
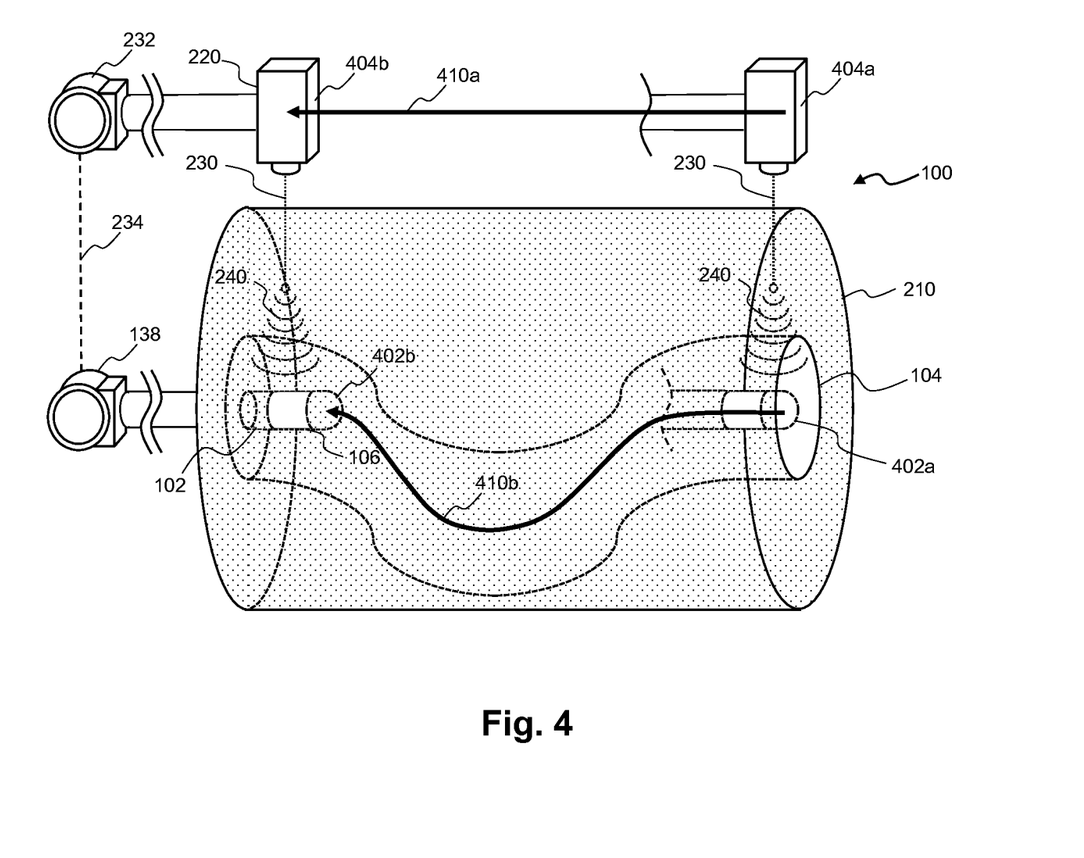
FIG. 4 is a diagrammatic, perspective view of a convoluted vascular pathway and surrounding tissue with an instrument moving within the pathway and a moving external emitter according to an embodiment of the present disclosure.

FIG. 4 depicts a measurement apparatus 102 disposed within a convoluted vascular pathway and an external optical emitter 220. The optical emitter 220 and measurement apparatus 102 are moved synchronously. In the example of FIG. 4, the synchronized movements of the optical emitter 220 and the measurement apparatus 102 are operable to allow photoacoustic waves to reach the optical emitter 220 at different locations along the vascular pathway. In particular, the actuator 232 drives the optical emitter 220 from first position 404a to second position 404b along the direction of travel 410a while the pullback device 138 moves the measurement apparatus 102 from first position 402a to second position 402b along the direction of travel 410b. In this case, unlike the example of FIG. 3, the direction of travel 410a of the optical emitter 220 is not exactly the same as the direction of travel 410b of the measurement apparatus 102. In particular, the direction of travel 410b of the measurement apparatus 102 is arcuate and longer than the direction of travel 410a due to the curves of the vascular pathway 104 that the measurement apparatus 102 must accommodate. Furthermore, the optical emitter 220 can travel at a lower velocity along the direction of travel 410a than the velocity at which the measurement apparatus 102 travels along the direction of travel 410b to account for the difference in path length. It is noted that in the example of FIG. 4, as in FIG. 3, photoacoustic waves 240 reach the sensor array 106 connected to the measurement apparatus 102 at the first position 402a and the second position 402b as well as intermediate positions therebetween. In particular, the velocity and direction at which the optical emitter 220 and the measurement apparatus 102 travel is operable to allow the measurement apparatus 102 to receive photoacoustic waves 240 along the mapping route.

Figure 5:
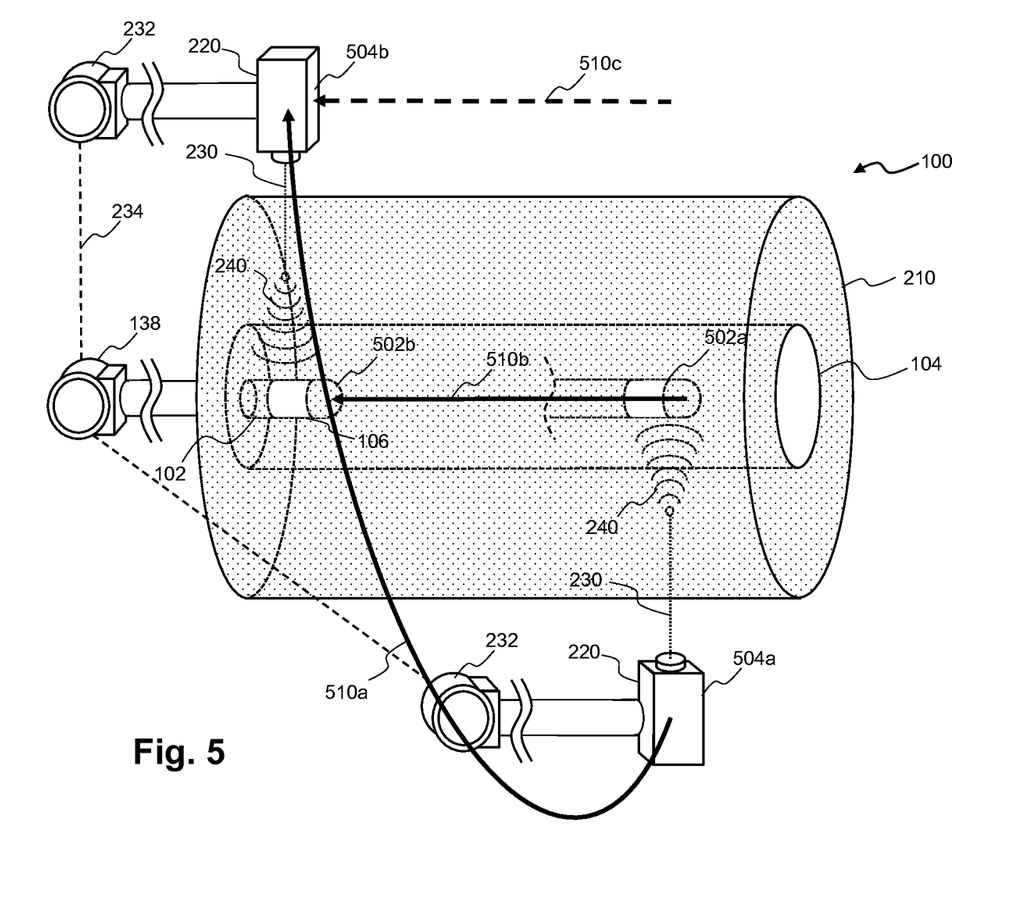
FIG. 5 is a diagrammatic, perspective view of a vascular pathway and surrounding tissue with an instrument moving within the pathway and a moving external emitter according to an embodiment of the present disclosure.

FIG. 5 depicts a measurement apparatus 102 disposed within a vascular pathway 104 and an external optical emitter 220. The optical emitter 220 and the measurement apparatus 102 are moved synchronously. In this example, the optical emitter 220 travels along an arcuate path revolving around a section of the body. In particular, the actuator 232 drives the optical emitter 220 from first position 504a to second position 504b along the arcuate direction of travel 510a while the pullback device 138 moves the measurement apparatus 102 from first position 502a to second position 502b along the direction of travel 510b. In the example of FIG. 5, the velocity and direction of travel 510a of the optical emitter 220 is not equivalent to the velocity and direction of travel 501b of the measurement apparatus 102. In particular, the arcuate direction of travel 510a is longer than the direction of travel 510b. Furthermore, the optical emitter 220 can travel along direction 510a at a higher velocity than the measurement apparatus 102 (which travels along direction 510b) to account for the difference in path length. An x-component 510c of the movement vector of the optical emitter 220 is depicted in FIG. 5 as being equivalent to the movement vector of the measurement apparatus 102. In some cases, the velocity of the optical emitter 220 in the direction of the x-component 510c is equal to the velocity of the measurement apparatus 102 in the direction 510b.

In the example of FIG. 5, the actuator 232 connected to the optical emitter 220 moves with the optical emitter 220. In some embodiments, the actuator 232 has a rigid connection to the optical emitter 220 and travels along a track or wire with the optical emitter 220. In other embodiments, the actuator 232 does not travel with the optical emitter 220 and may remain static during an operation. In some cases, one or more sensors 106 are configured or rotate around the measurement apparatus 102 in such a way so that the one or more sensors 106 face the optical emitter 220 at all times. Alternatively, the one or more sensors 106 are disposed circumferentially around the measurement 102 and do not rotate independently.

Figure 6:
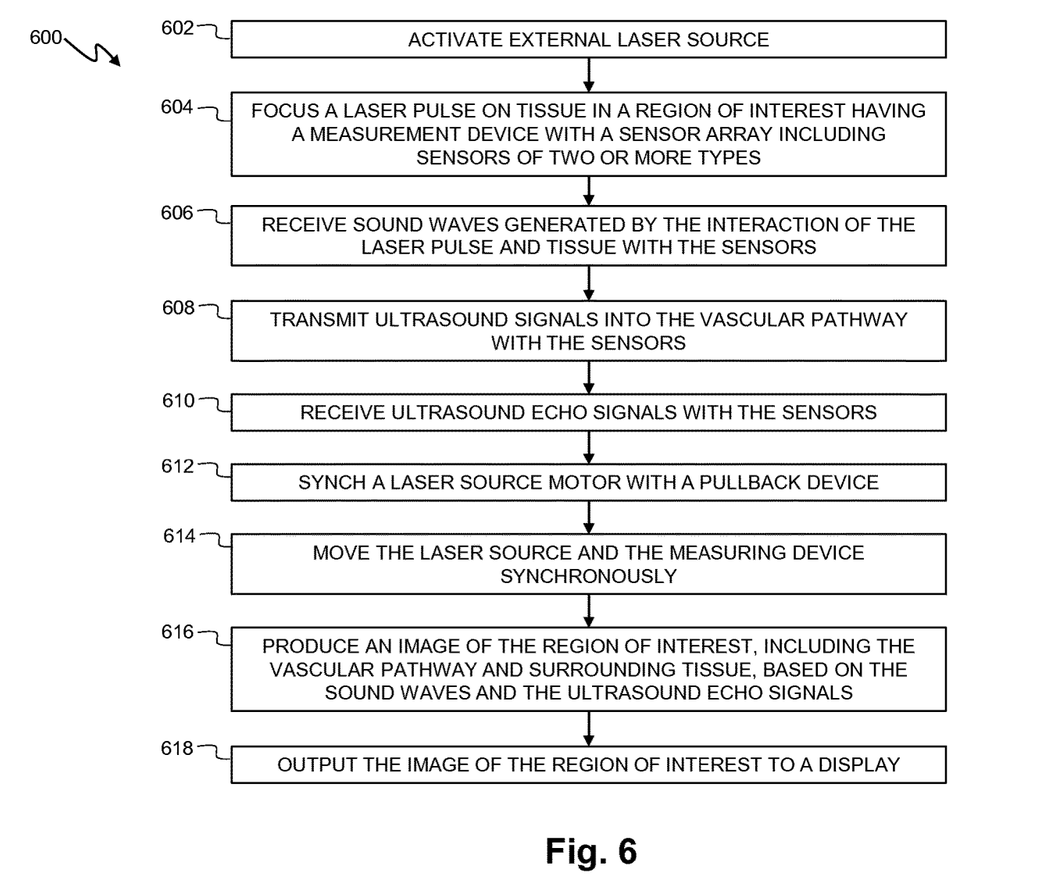
FIG. 6 is a flow diagram of a method for mapping a vascular pathway with photoacoustic and ultrasound modalities according to some embodiments of the present disclosure.

FIG. 6 is a flow chart showing a method 600 of mapping an area of interest using both photoacoustic and IVUS modalities. It is understood that additional steps can be provided before, during, and after the steps of method 600, and that some of the steps described can be replaced or eliminated for other embodiments of the method. In particular, steps 604, 606, 608, and 610 may be performed simultaneously or in various sequences as discussed below.

At step 602, the method 600 can include activating an external laser source. This laser source may be the optical emitter 220 of FIGS. 2-5. In some cases, the external laser source is activated by a communication system by means of an electronic or optical signal. This signal may be sent wirelessly, and the external laser source may be equipped with a wireless signal receiver.

At step 604, the method 600 can include focusing a laser pulse on tissue in a region of interest having a measurement device with a sensor array including sensors of two or more types. In some embodiments, the region of interest includes a portion of tissue including a portion of at least one vascular pathway 104. The measurement device may be disposed within the vascular pathway 104. The region of interest may be chosen based on a suspected or diagnosed problem in the tissue, or based on the proximity of a region of tissue to problems within a vascular pathway 104. In other embodiments, the region of interest is part of a more general mapping plan. For example, a mapping plan for a section of a vascular pathway 104 may involve the mapping of tissue surrounding the vascular pathway 104 along its length. The interaction of the emitted laser pulse and tissue in the region of interest may create a number of photoacoustic waves 240 that emanate from the tissue.

In some embodiments, the measurement device is the measurement apparatus 102 depicted in FIGS. 1A-1D or 2-5. The sensor array may be any of the sensor arrays 128 depicted in FIGS. 1C or 1D. In some embodiments, the sensors may be sensors 106 such as those depicted in FIGS. 1A-1D or 2-5, and can include IVUS transducers, photoacoustic transducers, optical emitters, and optical receivers. In some embodiments, the sensor array does not rotate as it travels through the vascular pathway 104. In other embodiments, the sensor array rotates around a transverse axis of the measurement device. The sensor array may be disposed on a revolving portion of the measurement device. In some embodiments, the sensors are disposed circumferentially around the measurement device.

At step 606, the method 600 can include receiving sound waves generated by the interaction of the laser pulse and tissue with the sensors. In some cases, the sensors can function with the traditional IVUS functionality to receive ultrasound waves. In other cases, some or all of the sensors are dedicated to receive photoacoustic waves. In some embodiments, the sensors are controlled by a communication system 250 like that depicted in FIGS. 3 and 4. In another embodiment, a processing engine 134 or a PIM 114 may control the sensors on the sensor array 128. Signals may be sent from processing engine 134 or the PIM 114 to the sensors via connector 234, causing the sensors to receive diagnostic information such as sound waves, ultrasound signals, and ultrasound echo signals.

At step 608, the method 600 can include transmitting ultrasound signals into the vascular pathway 104 with the sensors. Ultrasound signals may be transmitted toward the walls of the vascular pathway 104 and may be deflected off the walls of the vascular pathway 104 and propagate through the vascular pathway 104 as ultrasound echo signals.

At step 610, the method 600 can include receiving the ultrasound echo signals with the sensors. In some embodiments, the sensors may be operable to receive sound waves as well as ultrasound signals. The sensors of step 608 and the sensors of step 610 may be combined in a single sensor, or alternatively, the sensors may be separate.

At step 612, the method 600 includes synching a laser source actuator with a pullback device. The laser source actuator may be the actuator 232 of FIGS. 2-5, and the pullback device may be the pullback device 138 of FIGS. 1A, 1B, and 2-5. In some embodiments, the laser source actuator is connected to and operable to move the external laser source and the pullback device is connected to and operable to move the measurement device. Step 612 may include placing the laser source actuator and the pullback device in communication. Additionally or alternatively, the laser source actuator and the pullback device are controlled via signals sent from a control device.

At step 614, the method 600 includes moving the laser source and the measurement device synchronously. In some embodiments, the laser source and the measurement device are moved relative to each other such that photoacoustic waves reach the photoacoustic sensor at different locations along a mapping route. In some cases, the laser source is moved at the same velocity and direction of travel as the measurement device. In other cases, the laser source is moved at a different velocity and direction of travel as the measurement device, such as the case where the measurement device is moved along a convoluted path. The laser source and the measurement device may be moved so that they stay within a zone such that sound waves produced by the laser source may be received by the measurement device.

Steps 604, 606, 608, 610, 612, and 614 may be coordinated in the method 600 and occur in various orders based on the desired outcome of a medical procedure. For example, transmission of ultrasound signals and reception of ultrasound echo signals can occur at regular intervals throughout the method 600, while reception of photoacoustic waves may occur sporadically. This may be the case in a medical procedure to map a vascular pathway 104 and spot-check trouble areas of tissue surrounding sections of the vascular pathway 104. Furthermore, the steps 612 and 614 may occur during various orders of steps 604, 606, 608, and 610. For example, the laser source and the measurement device may be moved during the transmission and reception of signals. In some embodiments, steps 604, 606, 608, and 610 may be performed successively. For example, steps 604, 606, 608, and 610 may be performed successively before proceeding to the next step to avoid signal noise and allow for adequate signal processing. This may be the case when method 600 is used in a system where a photoacoustic sensor and an ultrasound transducer are each included in a transducer array. Furthermore, the steps of method 600 may be interleaved in various orders.

At step 616, the method 600 can include producing an image of the region of interest, including the vascular pathway 104 and surrounding tissue, based on the sound waves and the ultrasound echo signals. In some embodiments, a processing engine (such as the processing engine 134 of FIG. 1A) in communication with the sensors produces the image of the region of interest. This image can include both two-dimensional and three-dimensional images based on the received sensor data. In some cases, the image includes a number of two-dimensional cross sections of the vascular pathway 104 and surrounding tissue.

At step 618, the method 600 includes outputting the image of the region of interest to a display 118. This display 118 can include a computer monitor, a screen on a patient interface module (PIM) 114 or console 116, or other suitable device for receiving and displaying images.

In an exemplary embodiment within the scope of the present disclosure, the method 600 repeats after step 618, such that method flow goes back to step 602 and begins again. Iteration of the method 600 may be utilized to map a vascular pathway and surrounding tissue.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A medical sensing system comprising: a non-imaging optical emitter positioned outside of a body and configured to emit optical pulses to tissue in a region of interest inside of the body, wherein the non-imaging optical emitter is connected to an actuator; and a measurement apparatus separate from the non-imaging optical emitter, wherein the measurement apparatus is configured to be placed within a vascular pathway in the region of interest and receive photoacoustic sound waves generated by the tissue resulting from interaction of the optical pulses with the tissue, wherein the measurement apparatus is connected to a pullback device, wherein the actuator and the pullback device are configured to coordinate a first movement of the non-imaging optical emitter outside of the body and a second movement of the measurement apparatus within the vascular pathway such that photoacoustic sound waves generated by different parts of the tissue during the first movement of the non-imaging optical emitter are received by the measurement apparatus at different positions of the second movement of the measurement apparatus.

2. The medical sensing system of claim 1, wherein the measurement apparatus is configured to: transmit ultrasound signals; and receive ultrasound echo signals based on the transmitted ultrasound signals.

3. The medical sensing system of claim 2, further comprising a processing engine in communication with the measurement apparatus, the processing engine operable to produce an image of the region of interest based on the received photoacoustic sound waves and the received ultrasound echo signals.

4. The medical sensing system of claim 3, further comprising a display in communication with the processing engine, the display configured to visually display the image of the region of interest.

5. The medical sensing system of claim 1, wherein the actuator is in communication with the pullback device.

6. The medical sensing system of claim 1, wherein the actuator and pullback device move the non-imaging optical emitter and the measurement apparatus together.

7. The medical sensing system of claim 6, wherein the actuator and pullback device move the non-imaging optical emitter and the measurement apparatus together with synchronized first and second movements.

8. The medical sensing system of claim 1, further comprising a controller operable to control the actuator and the pullback device.

9. The medical sensing system of claim 8, wherein the controller is further operable to synchronize the first movement of the non-imaging optical emitter and the second movement of the measurement apparatus.

10. The medical sensing system of claim 1, wherein the measurement apparatus further comprises at least one ultrasound transducer configured to transmit ultrasound signals and receive ultrasound echo signals based on the transmitted ultrasound signals.

11. The medical sensing system of claim 10, wherein the at least one ultrasound transducer is further configured to receive the photoacoustic sound waves.

12. The medical sensing system of claim 11, wherein the measurement apparatus further comprises at least one photoacoustic transducer configured to receive the photoacoustic sound waves.

13. The medical sensing system of claim 12, wherein the at least one photoacoustic transducer and the at least one ultrasound transducer are configured to alternate in receiving the photoacoustic sound waves and the ultrasound echo signals.

14. The medical sensing system of claim 12, wherein the at least one photoacoustic transducer is disposed circumferentially around a distal portion of the measurement apparatus.

15. The medical sensing system of claim 12, wherein the at least one photoacoustic transducer is coupled to a drive member that rotates the at least one photoacoustic transducer around a longitudinal axis of the measurement apparatus.

* * * * *